United States Patent [19]
Lamport et al.

[11] Patent Number: 6,099,535
[45] Date of Patent: Aug. 8, 2000

[54] HYDRAULICALLY ACTUATED MULTIBAND LIGATOR

[75] Inventors: Ronald Lamport, Pelham, N.H.; Gregory Stiegmann, Denver, Colo.; Frank Van Patterson, Exeter, N.H.

[73] Assignee: C.R. Bard, Inc., Murray Hill, N.J.

[21] Appl. No.: 09/202,080

[22] PCT Filed: Jun. 6, 1997

[86] PCT No.: PCT/US97/11962
§ 371 Date: Mar. 19, 1999
§ 102(e) Date: Mar. 19, 1999

[87] PCT Pub. No.: WO97/46161
PCT Pub. Date: Dec. 11, 1997

Related U.S. Application Data

[60] Provisional application No. 60/019,207, Jun. 6, 1996.

[51] Int. Cl.⁷ .................................................. A61B 17/04
[52] U.S. Cl. ........................................... 606/140; 606/139
[58] Field of Search ...................... 606/139, 140

[56] References Cited

U.S. PATENT DOCUMENTS

| | | | |
|---|---|---|---|
| 5,318,544 | 6/1994 | Drypen et al. | 604/210 |
| 5,423,834 | 6/1995 | Ahmed | 606/140 |
| 5,507,797 | 4/1996 | Suzuki et al. | 606/140 |

FOREIGN PATENT DOCUMENTS

| | | |
|---|---|---|
| 67 93 68 | 2/1995 | European Pat. Off. . |
| 64 27 66 | 3/1995 | European Pat. Off. . |

*Primary Examiner*—Gary Jackson
*Attorney, Agent, or Firm*—Darby & Darby

[57] ABSTRACT

A hydraulically multiple ligating band dispenser comprising a body whose distal portion is adapted to support the elastic ligating bands. A tissue contacting surface is disposed surrounding and spaced from the distal portion so as to define a chamber. A seal slidably mounted on the distal potion is shaped to seal the chamber, to which a proximally situated fluid inlet is coupled. By these means pressurized fluid applied to the fluid inlet causes the seal to slide in a distal direction along the distal portion in order to urge the ligating bands distally and to dispense them serially.

19 Claims, 5 Drawing Sheets

HYDRAULICALLY ACTUATED MULTIBAND LIGATOR

This application claims benefit of provisional application 60/019,207 Jun. 6, 1996.

BACKGROUND OF THE INVENTION

1. Field of the Invention

This invention generally relates to ligating instruments and more particularly to instruments for dispensing a plurality of ligating bands to one or more internal sites within a patient's body in a single ligation procedure, without removing the instrument between successive ligating band placements.

2. Brief Description of Related Art

The treatment of various types of lesions including internal hemorrhoids and varices by ligation within the alimentary canal in order to stop bleeding is well known. The object of ligation is to position an elastic cord, or ligating band, at the lesion to stop circulation through tissue and allow the tissue to necrose whereupon the body sloughs off the necrotic or dead tissue.

Surgical ligation has also been employed in female and male sterilization procedures. In the case of tubal ligation in female patients, ligating rings or bands are placed on a folded-over loop portion of each Fallopian tube, blocking the path from uterus to ovaries, and thereby preventing fertilization of an ovum. In the case of male sterilization, a ligating band may similarly be placed on a folded-over loop portion of the vas deferens, thus preventing passage of spermatozoa from the testes.

The following United States Letters Patent disclose various embodiments of ligating instruments that are useful for dispensing a ligating band at a designated site within a patient: 3,760,810 to Van Hoorn; 4,257,419 to Goltner, et al.; and 4,735,194 to Stiegmann. Each of the foregoing instruments dispenses a single ligating band or a single set of ligating bands at a single location. None suggests dispensing ligating bands at discrete locations. The Van Hoorn patent does disclose the possibility of depositing plural ligating bands; however, Van Hoorn seems only to suggest dispensing plural ligating bands at a single site in a single operation. The apparatus disclosed in the Van Hoorn, Goltner or Stiegmann patents apparently would have to rely on an operator's sense of touch in order to displace the inner tube by an incremental distance corresponding to the thickness of a stretched ligating band to deposit a plurality of bands at different sites. That would be very difficult to accomplish. Thus, when it is desired to deposit ligating bands at different sites, the common practice has been to withdraw the entire instrument from the patient and load a new ligating band onto the inner tube. Loading ligating bands on an instrument requires special tools and could be time consuming particularly if the special tooling must be retrieved to install each ligating band individually while the instrument is withdrawn. Each of these instruments requires some structure, such as special stoppers or overtubes, for preventing the premature dispensing of the ligating band. Consequently, none of these instruments was readily adapted for dispensing ligating bands at different sites without withdrawing the instrument after each individual site is ligated.

Aimed at solving the aforementioned problems, the following United States Letters Patent disclose various embodiments of ligating instruments which are designed to deposit or place a plurality of ligating bands at one or more internal sites within a patient without the necessity of withdrawing the ligating instrument to reload successive ligating bands: 3,985,138 to Jarvik; 4,226,239 to Polk et al.; 3,870,048 to Yoon; 5,207,690 to Rohrabacher et al.; and 5,269,789 to Chin.

U.S. Pat. No. 3,985,138 to Jarvik discloses a ligature gun for placing a plurality of preformed suture loops which are tightened around bleeders after emplacement. The successive preformed suture loops are advanced to the dispensing end of the ligature gun by rotation of a threaded rod onto which the loops have been preloaded. The Jarvik ligature gun comprises large number of mechanical parts and is relatively complex in design and operation.

U.S. Pat. No. 3,870,048 to Yoon discloses the use of elastic bands or rings in tubal ligation. The Yoon device is constructed so as to permit two or more ligating rings to be loaded at the same time, but discharged separately at different times and in succession to one another, even at different locations, all without removing the ligating device from the patient's body cavity. Yoon's device is also relatively complex.

U.S. Pat. No. 4,226,239 to Polk et al. also describes a surgical ligating instrument for tubal ligation within a human or animal body, by the application of two or more elastic ligating rings without the necessity of removing the instrument from the patient for each ligating ring. In the device of Polk et al., a number of ligating rings are stretched over a cylindrical shaft which is slidably and concentrically received within an outer cylindrical sleeve. As the cylindrical shaft is withdrawn proximally with respect to the outer sleeve, the outer sleeve successively forces the ligating rings off of the shaft, preferably one at time. The extent of relative motion between the shaft and the sleeve is controlled by a mechanical stop at the proximal end of the shaft, located in the pistol handle of the instrument. The operator can be sure that a only single band has been placed only if the mechanical stop is precisely calibrated to the width of an individual ligating ring. The ligator disclosed by Polk et al. requires the molding of several separate components of a manufacturing tolerance sufficiently precise to not permit the elastic band to be pinched or caught between the sleeve and shaft. U.S. Pat. No. 4,860,746 discloses a device similar to that of Polk et al., and similarly requires precise manufacturing tolerances.

U.S. Pat. No. 5,207,690 to Rohrabacher et al. teaches that successive ligating rings may be slipped off of the cylindrical shaft onto which they have been preloaded by the use of separate forceps.

U.S. Pat. No. 5,269,789 to Chin et al. discloses a ligating band dispenser located at the distal end of an elongated introducer, which dispenser responds to manipulation of an operating structure at the proximal end of the introducer. The dispenser comprises first and second coaxially located, interfitted segments that support ligating bands at a plurality of axially spaced positions thereon. Each segment includes a spaced ligating band engagement structure for engaging portions of each ligating band or set of bands. One of the segments connects to the operating structure for being moved between first and second positions relative to the other of the segments. This motion dispenses one of the ligating bands from the distal end of the ligating instrument and moves the remaining ligating bands distally with respect to the dispensing means thereby to position a successive ligating band for being dispensed at a different site, as in some of the aforementioned devices as well. The Chin et al. instrument, however, is an improvement over those devices in that it is specially constructed to prevent more than a single ligating band from being dispensed in response to a single actuation of the operating structure. On the other hand, the ligating bands are initially greatly stretched when loaded onto the Chin et al. instrument, bringing about the necessity of a relatively strong spring in order to slide the bands distally. The operator's hand must work against this spring when actuating the device. Moreover, advancement of the ligating bands toward the dispensing end of the device requires the bands to be stretched even further than their initial stretched conditions. Such stretching requires even greater force to applied by the operator's hand. U.S. Pat. No. 5,356,416 to Chu et al. discloses a device similar to Chin et al. further including a sclerotherapy needle for administering a sclerotherapy agent as an alternative to ligating a lesion.

U.S. Pat. No. 5,398,844 describes a multiple band ligator which is currently being introduced to market. The Wilson Cook "Six-shooter," product no. MLV-6, which is based on an invention by Mr. Munir Ahmed of DabeGran Technologies, is also a multiple band ligator which is being introduced to the market. These devices overcome the limitations of single band ligation because they can deploy multiple bands (6 and 5 bands respectively) without removal of the scope from the patient. Neither design requires the use of an overtube which further reduces the risks of esophageal tears and perforations associated with endoscopic procedures. However, these products utilize draw strings which are tensioned upon application of a pulling force via a trigger. These draw strings or tensioners are contained within a conduit which runs the length of the working channel of the endoscope. The space occupied by the conduit inhibits the suction irrigation that occurs within the working channel. The blood in the working channel inhibits the field of view and thereby tends to lengthen the time of the procedure and increase the difficulty to the operator. The device according to the '844 patent, for example, is believed to decrease a 2.8 mm working channel by 42%. Further, each of these devices requires intricate manual assembly of the bands, the individual trip lines, and the external actuating mechanism for releasing the bands.

OBJECTS AND SUMMARY OF THE INVENTION

Therefore, it is an object of this invention to provide an instrument that can dispense plural ligating bands in sequence at discrete sites.

Another object of this invention is to provide a ligating instrument that can deposit plural ligating bands in sequence without requiring the instrument to be removed from a patient after each ligation.

Still another object of this invention is to provide a ligating band dispenser for attachment to diverse introducer structures including rigid and flexible endoscopes for ligating tissue.

The present invention permits multiple band firing without the need to retracting, reloading, and reinserting the dispenser. As a result, reintubation is required only after several ligating bands have been fired. Generally, a single intubation with the ligating band dispenser of the present invention is sufficient to ligate the tissue at least one internal tissue site within a patient's body. This affords a savings in time and reduces patient discomfort during the procedure.

According to the invention, a ligating band dispenser located at the distal end of an elongated introducer responds to hydraulic pressure which is applied through a hydraulic line from the vicinity of the proximal end of the introducer. The dispenser supports a plurality of elastic ligating bands on a band supporting surface of the device in a stretched condition. A tissue contacting surface surrounds the band supporting surface in spaced relation thereto, thereby defining an annular channel therebetween. The tissue contacting and band supporting surfaces may together comprise a unitary assembly having a proximal end adapted to frictionally couple the device to an endoscope or proctoscope. The ligating device includes a fluid port at its proximal end for attachment to a hydraulic line which preferably extends external the endoscope or proctoscope. A dynamic seal is disposed on the band support surface, just distal to the fluid port, yet proximal to the supported elastic bands. Application of hydraulic pressure through the hydraulic line to the fluid port causes the elastic bands to be serially dispensed. Preferably, the distal end of the tissue contacting surface extends distal to the band supporting surface and has a radiused distal end to provide an atraumatic tissue contacting tip and to define a band release aperture dimensioned to permit only one elastic band to pass through. According to this construction, one or more ligating bands may be independently dispensed onto tissue at one or more designated sites thereby accomplishing ligation thereof.

An apparatus according to the invention may be configured to dispense a predetermined volume of fluid to the dispenser. Such a configuration causes a metered dose of fluid to be advanced to the dispenser that is sufficient to displace a single elastic band from the dispenser. A subsequent dose of fluid causes the next band to be dispensed, and so on, with a single band being dispensed with each actuation of the fluid delivery device.

These and other features and advantages of the invention will be readily apparent from the following detailed description of certain embodiments taken in conjunction with the accompanying unscaled drawings.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DETAILED DESCRIPTION OF A PREFERRED EMBODIMENT

Figure 1:
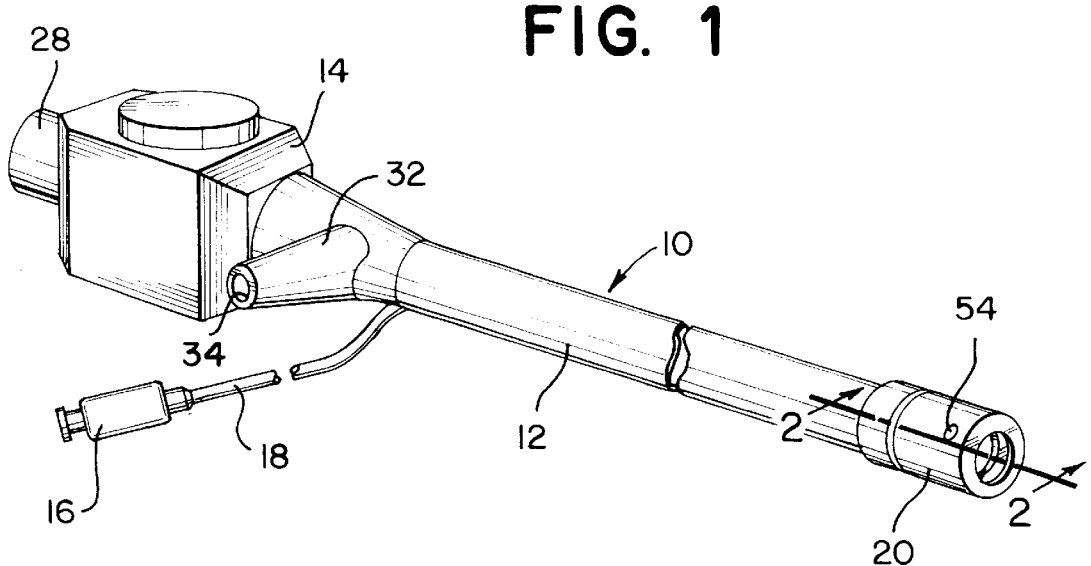
FIG. 1 is a perspective view of an endoscope upon which is mounted a ligating band dispenser constructed in accordance with this invention.

By way of overview and introduction, FIG. 1 depicts, in perspective view, an embodiment of an ligating instrument 10 that serially dispenses elastic ligating bands during a succession of operations by a operator. The ligating instrument 10 generally includes an introducer in the form of an elongated, rigid tubular housing 12. Disposed in the vicinity of a proximal end portion 14 of the instrument 10, is a luer fitting 16 attached to a hydraulic line 18. The hydraulic line 18 extends distally, preferably along side the exterior of the ligating instrument 10, to a dispenser 20 constructed in accordance with the invention. Preferably, the dispenser 20 is configured as an attachment to the ligating instrument 10, for example by a frictional engagement of the proximal end 22 of the dispenser and the distal end 24 of the ligating instrument 10 (see FIG. 2). It should be understood, however, that the ligating instrument 10 can be any variety of elongated instruments including, for example, an endoscope or proctoscope or a dedicated instrument for ligation, or with shorter instruments such as an anoscope.

The luer fitting 16 is adapted to connect to a fluid delivery device 60, such as a syringe so that an aliquot or controlled dose of fluid can be delivered through the hydraulic line 18 to the dispenser 20. Where the fluid delivery device 60 is a syringe, its plunger 80 (see FIG. 6) may be advanced by a threaded piston (not shown) or by a keyed piston (as shown). As described more fully hereinbelow, delivery of an aliquot of fluid to the dispenser 20 causes a ligation band 26 to be dispensed by the instrument 10. The housing 12 is formed in a hollow tubular form to provide a central or axial passage that communicates a proximal vacuum connection 28 to the distally mounted ligature dispenser 20 so that tissue can be aspirated into the distal end 30 of the dispenser 20 (see FIG. 4) for ligation thereof (see FIG. 5).

The ligating instrument 10 is illustrated as having a proximal side access port 32 to a working channel 34. In the preferred embodiment, the working channel is not used to house the hydraulic line 18, and thereby permits maximum suction through the central lumen of the instrument. Instead, the hydraulic line 18 extends along side the instrument 10. Alternatively, the hydraulic line 18 could be located within the working channel if such an arrangement were desired. None of these arrangements affects the scope of the present invention, which is directed to the construction and operation of dispenser 20 itself.

The ligating instrument 10 or a conventional endoscope may further include means for providing visualization of internal body tissue distal of the dispenser 20, such as a conventional fiber optic and lens arrangement (not shown) or the like. In use, such visualization means generally assists the operator in guiding the dispenser 20 to the desired tissue site to be ligated.

According to one aspect of the invention, the ligating bands 26 are successively dispensed by application of hydraulic pressure. The dispenser 20 frictionally fits over the distal end 24 of a flexible endoscope 10 for the purpose of delivering elastic bands to a varix or a hemorrhoid within the alimentary canal in order to stop bleeding. Preferably, the dispenser 20 is transparent, about 0.5 inches in diameter, and projects from the end of the endoscope 10 by about 0.5 to about 0.75 inches. The dispenser 20 receives hydraulic pressure via the hydraulic line 18 which can be less than about 0.125 inch in diameter yet still provide sufficient pressure to serially dispense the ligating bands 26. The hydraulic line 18 preferably extends along side the exterior of the endoscope 10 and which is held captive thereto by tape or other conventional attachment means.

The hydraulic line 18 terminates at its proximal end with a luer fitting 16 which permits connection to a pressurized fluid delivery device (see FIGS. 6–11) such as a syringe, meterable dispenser, a pressurized gas canister, a roller pump, a piston compressor, or other delivery device capable of generating pressure on the hydraulic fluid. The fluid delivery device should be designed to deliver an aliquot or dose of fluid of predetermined size, for example, approximately 0.075 cc of fluid, from a fluid supply. The fluid may be, for example, saline.

Figure 6:
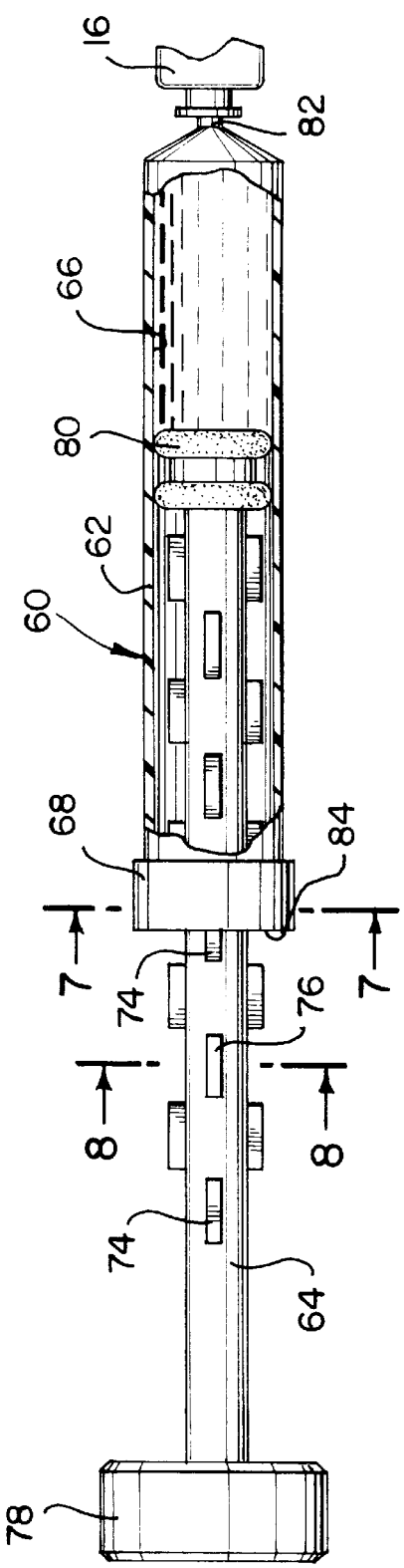
FIG. 6 is an exploded view of a fluid dispenser according to one aspect of the invention, adapted to dispense a predetermined volume of fluid.
Figure 8:
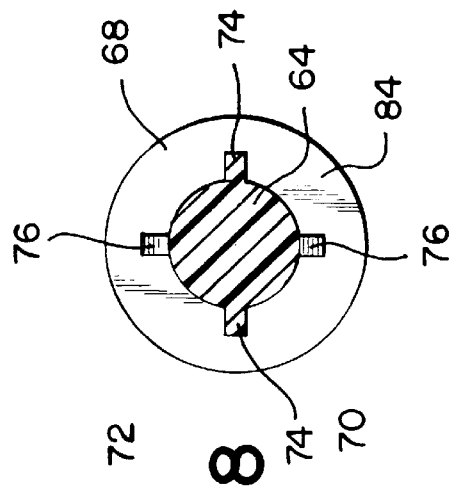
FIG. 8 is a cross-sectional view of the piston taken along lines 8—8 of FIG. 6.
Figure 7:
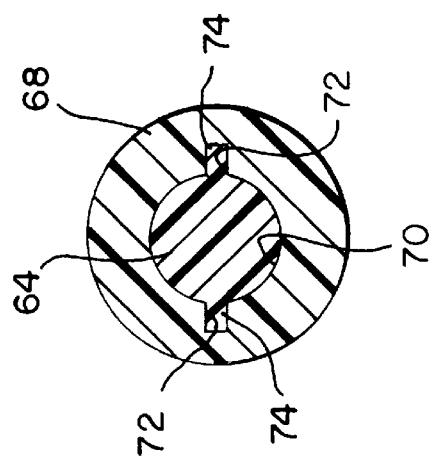
FIG. 7 is a top plan view of the fluid dispenser, taken along lines 7—7 of FIG. 6, the piston being omitted for clarity.
Figure 9:
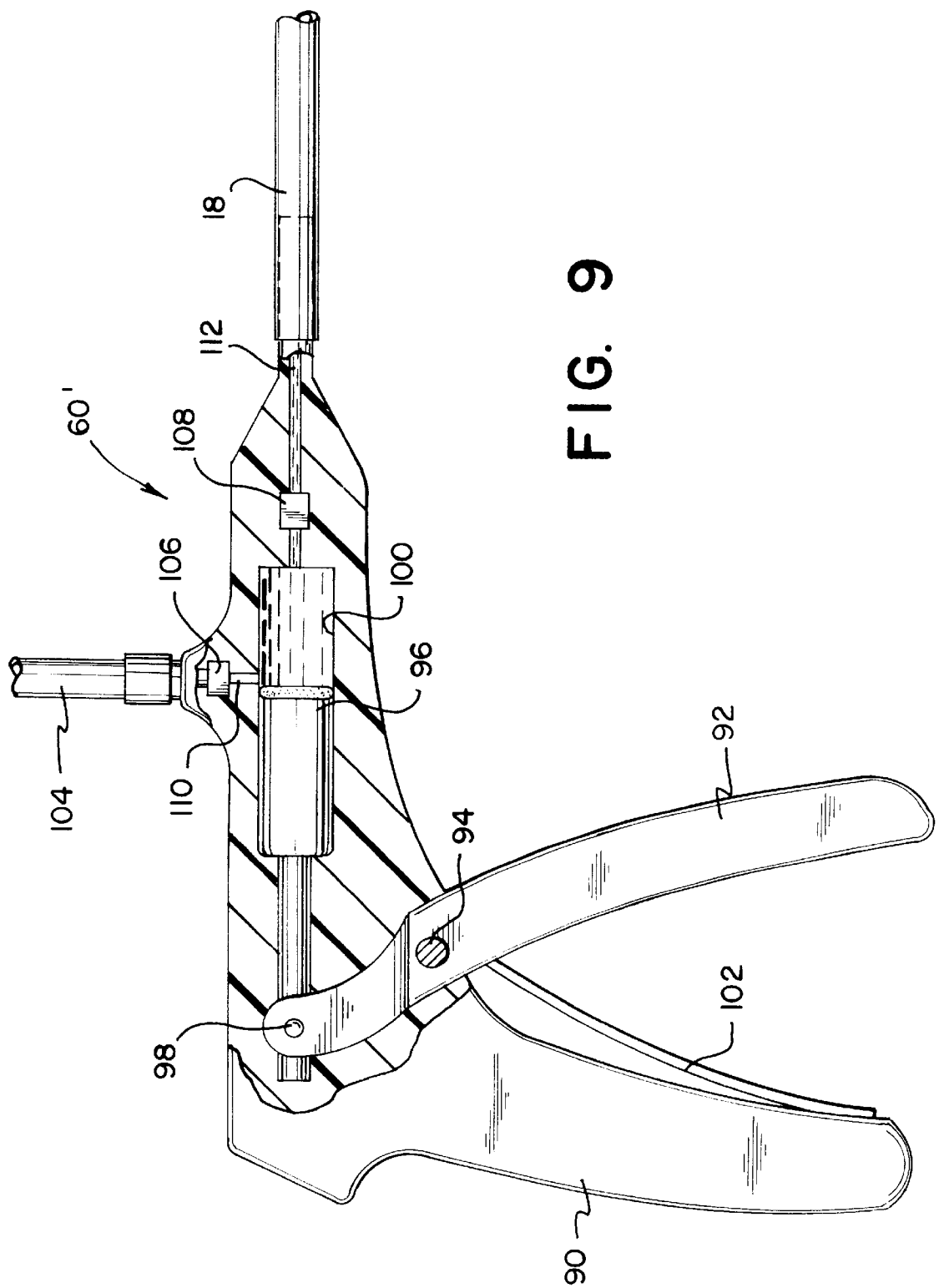
FIG. 9 is a schematic view of a fluid dispenser according to another aspect of the invention.
Figure 10:
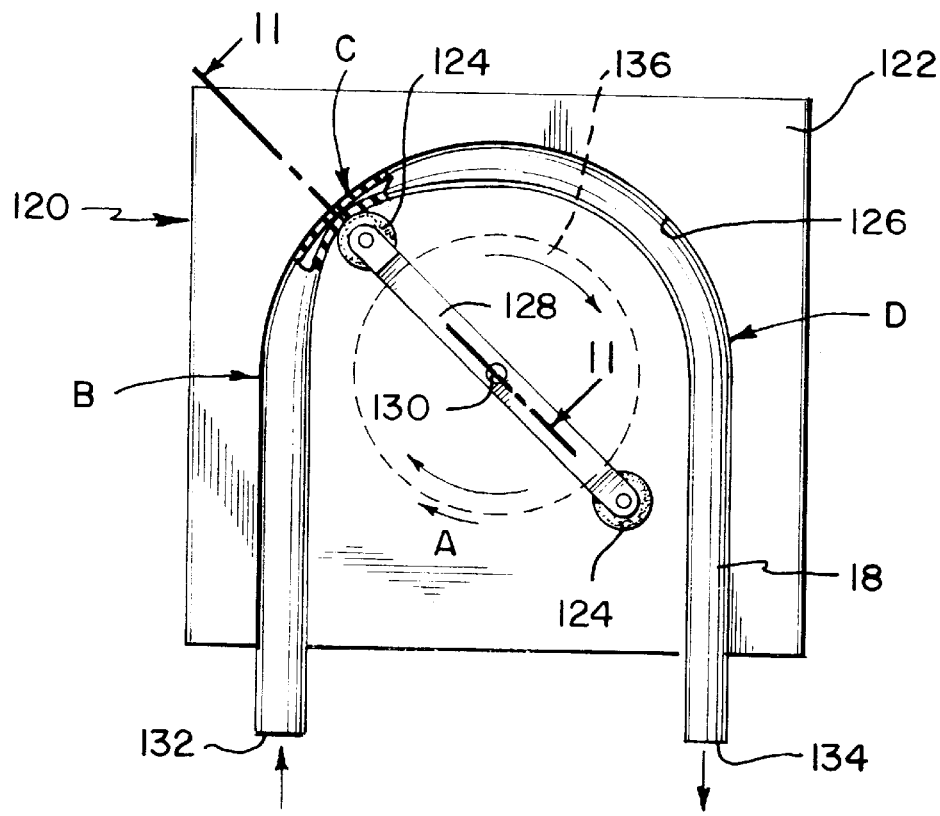
FIG. 10 is a top plan view of a fluid flow regulator according to yet another aspect of the invention.
Figure 11:
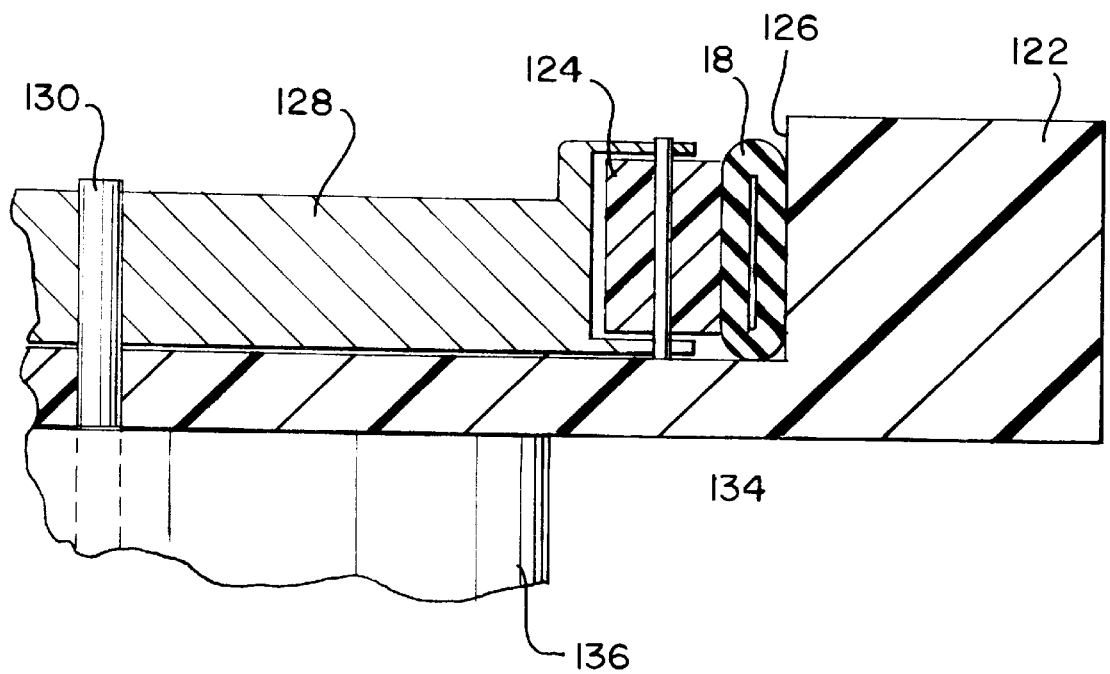
FIG. 11 is a cross-sectional view of the fluid flow regulator of FIG. 10, taken along lines 11—11.

The ligating bands 26 are preferably elastic "O"-shaped rings, fired or ejected by a pressurized, closed, hydraulic system which includes the dispenser 20, the hydraulic fluid delivery line 18, and a pressurized fluid delivery device 60 (e.g., the syringe of FIGS. 6–8 or one of the other devices shown in FIGS. 9–11). Regardless of the particular form of the fluid delivery device 60, the inventive system permits increments of hydraulic fluid to be dispensed so as to push the driving piston 44 forward (and thereby cause a single elastic "O"-shaped ring or band 26 to be ejected with each increment of hydraulic fluid in a measured and repeatable manner. The fluid delivery device 60, described below, can be constructed to deliver a metered dose of fluid, or a separate device may act on the hydraulic line 18 to restrict the volume of pressurized fluid that will advance toward the driving piston 44 upon opening and closing such device.

Figure 2:
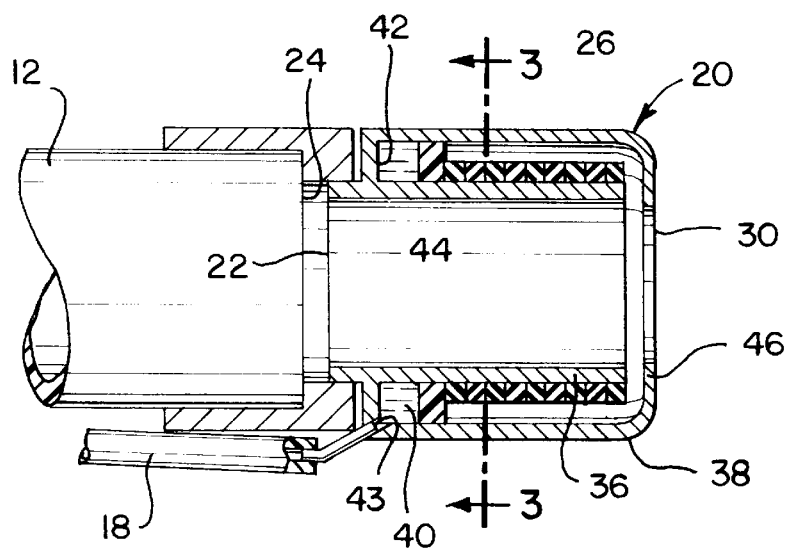
FIG. 2 is a sectional view of the dispenser in accordance with this invention, taken along line 2—2 of FIG. 1.

With reference now to FIG. 2, the dispenser 20 has a ligation band support surface 36 upon which a plurality of ligation bands 26 are mounted. The support surface 36 is preferably circular in cross section (see FIG. 3), and has a diameter relative to the ligating bands 26 such that the bands 26 are mounted in a stretched condition so that the bands will elastically return to a smaller diameter upon dispensing, thereby ligating the designated site. The dispenser 20 further has a tissue contacting surface 38 which is coaxial with the support surface 36 and spaced therefrom by a distance equal to at least the thickness of the ligation bands 26 when the bands are mounted in a stretched condition. The space between the support surface 36 and the tissue contacting surface 38 defines an annular chamber 40 which is sealed at wall 42 which connects the surfaces 36, 38 together as an unitary assembly. Adjacent the wall 42 is an inlet 43 for receiving fluid from the hydraulic line 18 upon application of pressure from the fluid dispensing device. The fluid enters the annular chamber 40 and urges a ring seal or cylindrical hydraulic piston 44 distally once the chamber 40 is full. The ring seal 44 stems the flow of fluid from escaping through the distal end 30 of the dispenser, and provides an abutment for serially urging successive ligating bands 26 off of the distal end 30 of the dispenser 20. Each aliquot of fluid preferably advances the ring seal 44 distally (along with the series of multiple bands) the distance of one band 26. This expels or fires the distalmost band 26 onto the aspirated tissue, varix, or hemorrhoid.

In order to reduce the likelihood of multiple bands 26 being deployed at once, the tissue contact surface 38 may be provided with a radially inwardly projecting annular rim 46 spaced from the distal end 30 by approximately the width of one ligating band 26 (as measured in the longitudinal direction) to define an annular space 48 which allows only one band 26 to pass. The annular rim 46 preferably projects radially inwardly toward the central axis of the ligating instrument 10 to a diameter of approximately 0.4 inches, but may only project inwardly to about the outer diameter of the support surface 36.

Figure 3:
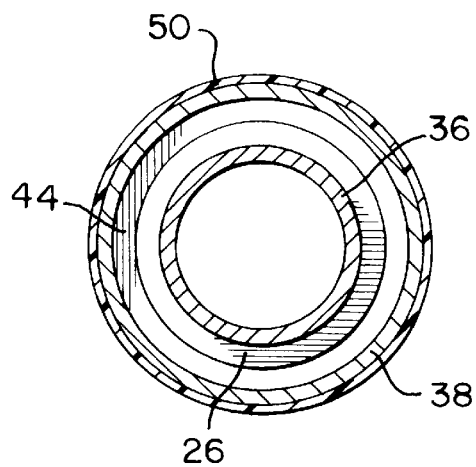
FIG. 3 is a cross-sectional view taken along lines 3—3 of FIG. 2.

The annular rim 46 preferably has a convex (radiused) outer contour to provide an atraumatic tissue contacting surface for entry (including intubation) and movement within the anatomy. The convex annular rim 46 minimizes abrasion, snagging, tearing, and scraping of the delicate tissue being treated. A low-friction coating 50 such as a moisture activated hydrophilic coating is preferably provided on the entire tissue contacting surface 38, 46 of the dispenser 20 (FIG. 3).

In FIGS. 6–11, described fluid delivery devices 60 of various forms are shown which, when actuated, controllably restrict the flow of fluid to the dispenser 20 so that only an aliquot or metered amount of fluid advances to the driving piston 44 of the dispenser 20. These devices may be disposed at one end of the hydraulic line 18, as shown in FIGS. 6–9, or along the line, as shown in FIGS. 10–11.

Turning now to FIGS. 6–8, a positive displacement fluid delivery device 60 is shown which takes the form of a syringe. The syringe includes a hollow barrel 62 having an internal fluid chamber defined by inner cylinder wall 66. The piston 64 is received at a proximal end of the barrel 62 through an end cap 68. As shown in FIG. 7, the end cap 68 has a central opening 70 which receives the piston 64, and a keyed opening 72 which receives radially outward projections or splines 74, 76 that extend from the piston 64 to regulate the amount of fluid dispensed from the syringe in a single actuation. The piston has a handle 78 at its proximal end, and a plunger 80 at its distal end which makes a fluid-tight seal with the inner cylinder wall 66. At the distal end of the barrel 62, a nozzle or outlet 82 permits pressurized fluid to exit the barrel's fluid chamber and advance through the hydraulic line 18 in conventional manner.

The projections 74, 76 are longitudinally and laterally offset from one another along the piston 64. Only when the projections that are immediately adjacent the end cap 68 are aligned with the keyed opening 72 can the piston 64 advance distally through the end cap 68 and thereby advance the plunger 80 relative to the barrel 62 to dispense fluid from the syringe 60. Once aligned, the piston 64 will continue to advance distally until the next projection abuts the end cap 68. However, until the piston 64 is rotated, it will not advance further due to the rotational offset of the next projection. In FIG. 6, projection 74 is aligned with the keyed aperture 72 and so the piston 64 can advance distally (to the right in FIG. 6) until projection 76 abuts the top rim 84 of the end cap 68. FIG. 8 illustrates one possible arrangement of projections 74, 76 about the piston 64 in which each of the projections 74 and 76 is provided in pairs that extend from opposing sides of the piston 64, and in which the projections 74 and 76 are generally orthogonal to one another. Other arrangements are possible, the important feature being that advancement of the piston 64 relative to the barrel 62 requires successive keying operations, between each of which the flow of fluid from the nozzle 82 is limited to a predetermined volume.

FIG. 9 illustrates the fluid delivery device 60' in the form of a positive displacement piston pump. Specifically, the fluid delivery device 60' includes a handle 90 to which a trigger 92 is pivotally connected about a pivot point 94 to drive a piston 96 through a coupling 98 between the trigger 92 and the piston 96. The piston 96 is disposed within a pump chamber 100 of the handle 90. A biasing spring 102 biases the piston into a first position in which fluid from a reservoir 104 flows into the pump chamber 100 past an inlet check valve 106. An outlet check valve 108 also communicates with the pump chamber 100; however, the outlet check valve 108 remains closed until the piston 96 compresses the fluid in the fluid chamber 100, that is, until the trigger 92 is actuated which causes the piston 96 to advance toward the outlet check valve 108 (to the right in FIG. 9). As the piston advances to the right, it seals off a fluid inlet 110 on the fluid chamber side of the inlet check valve 106, and forces fluid from the fluid chamber 100 through the outlet check valve 108 and out a nozzle 112 connected to the proximal end of the hydraulic line 18. Therefore, upon actuating (squeezing) the trigger 92, a predetermined volume of fluid is dispensed from the fluid delivery device 60' through the hydraulic line 18 and to the dispenser 20 to advance the piston 44 and dispense a single ligating band, and the biasing spring then forces the trigger 92 (and piston 96) to the first, rest position in which the pump chamber 100 refills with fluid from the fluid reservoir 104.

It is possible that an operator may fail to fully depress the trigger 92 which would result in a smaller, unspecified volume of fluid being dispensed. To better ensure that the piston 96 is fully displaced with each actuation, the actuation may be automated or arranged to move the piston 96 only after full movement of the trigger, for example, on the return stroke of the trigger 92 after it has been fully actuated (squeezed). This can be achieved using conventional mechanical techniques, as understood by those of skill in the art.

FIGS. 10 and 11 illustrate a fluid flow regulator 120 that may be connected to a fluid reservoir (and together comprise a fluid delivery device 60") to regulate or meter the volume of fluid provided to the dispenser 20. The regulator 120 includes a housing 122 which supports the hydraulic line 18 (or other collapsible tube in fluid communication therewith) between a roller 124 and a race 126 (see FIG. 11). The roller 124 is attached to a roller arm 128 which rotates about a center point 130 in the direction of arrow A. As the roller arm 128 rotates about center point 130, it presses the hydraulic line 18 against the race between points B, C, and D (point C is the point illustrated where the hydraulic line is compressed between the roller 124 and the race 126). The hydraulic line 18 is filled with fluid, supplied through inlet 132 from a fluid supply, but is ordinarily not under pressure. However, during the time that the hydraulic line 18 is compressed between the roller 124 and the race 126, pressure in the line 18 is increased and fluid advances in the direction of outlet 134 toward the inlet 43 of the dispenser 20 to cause the piston 44 to move. At all other times, the fluid pressure within the hydraulic line 18 is insufficient to move the piston 44 of the dispenser 20. Accordingly, the length of the race 126 that causes compression of the hydraulic line 18 (the arc spanning points B, C, and D) and the lumen diameter of the hydraulic line 18 are selected such that a predetermined and desired amount of fluid is dispensed with each rotation (or partial rotation) of the roller arm 128. As a result, the piston 44 advances a distance sufficient to dispense only one elastic band 26. A motor 136 may be used to drive the peristaltic pump, or it could be manually actuated, as understood by those of skill in the art.

Alternative arrangements for the fluid delivery device are possible. For example, a momentary, normally-closed valve which can be set to open for a preset time and thereby allow a known volume of fluid to pass through the valve can be used. The important design feature for the fluid delivery device is that only incremental volumes of fluid be advanced toward the fluid inlet 43 of the dispenser 20 in response to actuation of the delivery device.

The inventive dispenser 20 combines several distinct features which collectively make it a superior, unique and effective device compared to known existing devices. The dispenser 20 can dispense one band 26 at a time, can accommodate more than 5 or 6 bands without reloading, and will fire bands regardless of position of tip 24 of instrument 10. There is no structure that obstructs the operator's view through the viewing channel of the instrument 10. The dispenser 20 may be mounted onto instruments of various different widths (e.g., 9 mm to 15 mm diameter scopes), and may be mounted by a simple compression or friction fit. Because in the preferred embodiment the hydraulic line extends external to the instrument 10, the construction provides maximum suction to the distal end 30 of the dispenser 20 for clearing blood and aspirating tissue. Moreover, the inventive dispenser 20 is simple to operate and is inexpensive to manufacture (due to the low number of components that need to be molded).

Some dispensers that are currently in use fire only one band. These dispensers must be withdrawn from the patient and reloaded after each firing. This consumes valuable time insofar as the scope must be removed, reloaded, reinserted, and relocated to the site of interest. Each time the patient experiences these steps, he or she experiences discomfort. This is especially annoying to the patient where 3 to 8 bands are needed to stop bleeding areas. However, this invention, enables the delivery of a ligating band 26 to multiple locations without the need to withdraw the instrument 10 for reloading.

As a further optional feature, the distal end 30 of the dispenser 20 may be provided with an aperture 54 (see FIG. 1). Once the last ligating band 26 has been dispensed, the aperture 54 serves to provide an alternate, preferred fluid path for any additional aliquots of fluid that may be provided to the dispenser 20. This alternate path prevents the ring seal 44 from inadvertently being expelled from the dispenser 20 by fluid pressure which would otherwise cause further distal advancement of the ring seal 44. The aperture may be provided in either of the support surfaces 36 or 38.

Prior to use, the dispenser 20 is removed from its package and a saline filled syringe or other fluid delivery device is attached to the distal end of the hydraulic line 18 and saline is introduced into the tubing and device chamber and the air is expelled from the system. The dispenser 20 then may be mounted to the distal end of an endoscope 10. The hydraulic line may be secured to the exterior of the endoscope 10 with low friction removable tape or a close fitting sheath (not shown). The endoscope then may be introduced into the patient with or without an overtube.

Figure 4:
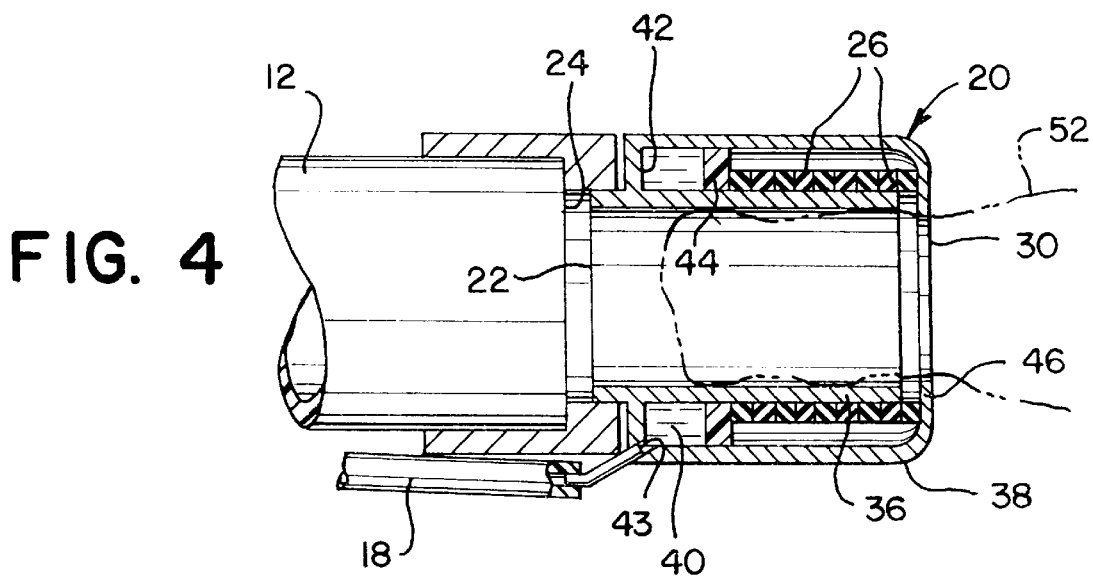
FIG. 4 is a sequential view of FIG. 2 taken at a moment just prior to dispensing a ligating band.
Figure 5:
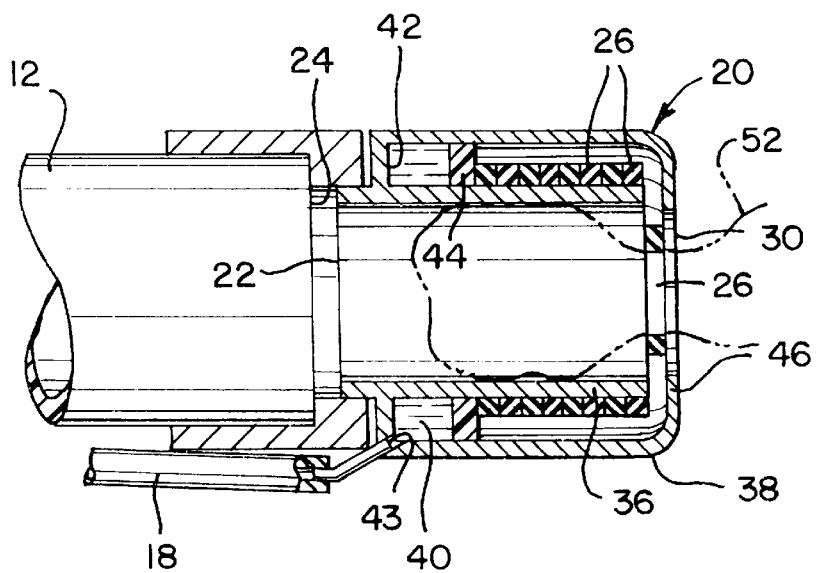
FIG. 5 is a sequential of FIG. 2 after having dispensed a ligating band.

With reference now to FIGS. 3, 4, and 5, the operation of the dispenser 20 is described. The ligating instrument is navigated through the patient to the designated site in a conventional manner. The tissue 52 at the designated site is then aspirated into a central cavity of the dispenser 20 (which channel communicates with the vacuum applied to port 28 of the ligating instrument), as illustrated in FIG. 4. The transmission of pressurized fluid from the fluid delivery device 60 (or 60' or 60" or any other equivalent device capable of delivering a controlled volume of fluid) attached to the luer fitting 16, through the hydraulic line 18 to the dispenser 20 causes the chamber 40 to fill. Once the chamber 40 is filled, the ring seal 44 is urged distally toward the distal end 30 of the dispenser 20 by the pressure of the fluid from the position illustrated in FIG. 3. The ring seal 44 abuts the most proximal one of a series of ligating rings 26. The distal movement of the ring seal 44 causes the series of ligating rings 26 to slide distally. The distal most one of the ligating rings 26 ultimately clears the distal end 30 of the dispenser 20, as illustrated in FIG. 4. At the moment that the distalmost mounted ligating ring 26 clears the distal end 30, the ring elastically snaps or restores itself to a reduced diameter, thereby ligating the aspirated tissue 52, as illustrated in FIG. 5. As each ligating band 26 is dispensed, the field of view is increased.

The embodiment shown in FIGS. 1 through 5 disclose a ligating band dispenser for a ligating instrument. The dispenser can dispense a single ligating band at a given location, or multiple ligating bands at a single location, or one or more bands at different locations. The operator may perform multiple ligating operations at different locations without having to withdraw the ligating instrument after each ligating band is dispensed. The support surfaces 36, 38 need not be cylindrical. Support surfaces of varying cross-sections may be provided, for example, square, rectangular, triangular, etc.

While line 18 has been described as a hydraulic line, it need not be. It may instead be a pneumatic line or a hybrid of gas and liquid under pressure. The term "fluid" is used herein in its broad sense of including both liquids and gases.

The foregoing embodiments have been described with respect to certain presently preferred dimensions that provide a dispenser that is suitable for deploying ligating bands 26 on any soft tissue in conjunction with an endoscope, for example, varices in the fundal region or stomach lining, or certain sized varices or internal hemorrhoids. However, other dimensions may be more particularly suitable for ligating a particular varix, internal hemorrhoid, or internal body structure or duct, as the case may be. Accordingly, the present invention is not limited in its utility to the foregoing dimensions.

Although this structure has been shown with respect to a particular ligating instrument 10, it will be apparent that a dispenser 20 constructed in accordance the disclosed embodiment is readily adaptable for connection with a wide variety of structures including those based upon rigid or flexible endoscopic structures, as previously mentioned herein. It will also be apparent that the dispenser 20 may be molded as a unitary part and is therefore reliable, readily producible, and structurally sound.

The ligating instrument is simple to use because it is merely necessary for the operator to position the ligating instrument and then apply hydraulic pressure to the hydraulic line 18. There is no need for the operator to sense the amount of travel required for depositing a single ligating band or a single set of ligating bands, because the amount of fluid being dispensed (and its compressibility) can be calculated and controlled to ensure that the aliquot dispensed causes a single band to deploy or fire.

While this invention has been disclosed in terms of a particular embodiment, it will be apparent that many modifications can be made to the specifically disclosed apparatus without departing from the invention. Therefore, it is the intent of the appended claims to cover all such variations and modifications as come within the true spirit and scope of this invention.

What is claimed is:

1. A ligating band dispenser for dispensing a plurality of elastic ligating bands onto at least one internal tissue site within a patient's body, comprising:

a body having a proximal portion and a distal portion, the distal portion being adapted to support the plurality of elastic ligating bands;

a tissue contacting surface disposed in surrounding relation to said distal portion and spaced therefrom so as to define a chamber therebetween;

a seal slidably mounted for distal movement only on said distal portion and shaped to seal said chamber;

a fluid inlet proximal to said seal and communicatively coupled with said chamber, whereby pressurized fluid applied to said fluid inlet causes said seal to slide distally along said distal portion to urge the plurality of elastic ligating bands distally and serially dispense the ligating bands.

2. A ligating band dispenser as in claim 1, further comprising a line having a distal end connected to said fluid inlet.

3. A ligating band dispenser as in claim 1, wherein said proximal end of said body is shaped to mount to a distal end of an elongated instrument.

4. A ligating band dispenser as in claim 3, wherein said elongated instrument is flexible.

5. A ligating band dispenser as in claim 1, wherein said body and said tissue contacting surface are made of a material which is transparent.

6. A ligating band dispenser as in claim 1, wherein said body has a support surface upon which the plurality of elastic ligating bands are supported, said support surface having a diameter relative to the plurality of elastic ligating bands such that the plurality of elastic ligating bands are mounted in a stretched condition.

7. A ligating band dispenser as in claim 6, wherein said tissue contacting surface is spaced from said support surface by a distance which is equal to at least the thickness of the ligation bands mounted on said support surface.

8. A ligating band dispenser as in claim 6, further comprising a radially inwardly projecting annular rim connected to said tissue contacting surface and spaced from a distal end of said support surface to define an annular space sufficient to allow only one ligating band to be dispensed at a time.

9. A ligating band dispenser as in claim 8, wherein said annular rim has a radiused outer contour to provide an atraumatic tissue contacting surface.

10. A ligating band dispenser as in claim 1, wherein said body, said tissue contacting surface, and said fluid inlet are integrally formed.

11. A ligating band dispenser for dispensing a plurality of elastic ligating bands onto at least one internal tissue site within a patient's body, comprising:

a body having a proximal portion and a distal portion the distal portion being adapted to support the plurality of elastic ligating bands;

a tissue contacting surface disposed in surrounding relation to said distal portion and spaced therefrom so as to define a chamber therebetween;

a seal slidably mounted on said distal portion and shaped to seal said chamber;

a fluid inlet proximal to said seal and communicatively coupled with said chamber, and a pressurized fluid delivery device connected in fluid communication with said fluid inlet of said body, said pressurized fluid delivery device comprises a syringe which includes:

a barrel having an internal fluid chamber;

an end cap adjacent one end of said barrel, said end cap having a central aperture and a keyed aperture;

a piston having a shaft which is received through said central opening in said end cap;

a series of projections along said piston which are adapted to be received in said keyed opening to permit insertion of said piston within said barrel when aligned therewith, adjacent ones of said projections being rotationally offset relative to one another, whereby pressurized fluid applied to said fluid inlet causes said seal to slide distally along said distal portion to urge the plurality of elastic ligating bands distally and serially dispense the ligating bands.

12. A ligating band dispenser as in claim 11, further comprising line having one end connected to said fluid inlet and another end connected to said pressurized fluid delivery device.

13. A ligating band dispenser as in claim 11, wherein said pressurized fluid delivery device is adapted, upon actuation, to deliver to said dispenser a predetermined volume of fluid from a fluid supply.

14. A ligating band dispenser for dispensing a plurality of elastic ligating bands onto at least one internal tissue site within a patient's body, comprising:

a body having a proximal portion and a distal portion, the distal portion being adapted to support the plurality of elastic ligating bands;

a tissue contacting surface disposed in surrounding relation to said distal portion and spaced therefrom so as to define a chamber therebetween;

a seal slidably mounted on said distal portion and shaped to seal said chamber; and a fluid inlet proximal to said seal and communicatively coupled with said chamber, wherein one of said body and said tissue contacting surface includes an aperture disposed so as to provide a fluid path for preventing pressurized fluid applied to said fluid inlet from causing said seal to be expelled from said dispenser, whereby pressurized fluid applied to said fluid inlet causes said seal to slide distally alone said distal portion to urge the plurality of elastic ligating bands distally and serially dispense the ligating bands.

15. A method of ligating tissue in a region of the alimentary tract of a patient, comprising the steps of:

(a) providing an instrument having a releasable ligating ring attached thereto and positioned distal to a seal mounted for distal movement only;

(b) inserting the instrument into the alimentary tract to a tissue site;

(c) abutting the lesion site with the portion of the instrument which has the releasable ligating ring attached thereto;

(d) providing a means for drawing the tissue into the instrument;

(e) drawing the tissue into the instrument for a distance; and (f) releasing the ligating ring from the instrument to effect the ligation by applying pressurized fluid from outside the patient to advance the seal distally to thereby dislodge the ligating ring.

16. A ligating method as in claim 15, wherein said instrument has plural releasable ligating rings attached thereto and wherein the step of applying pressurized fluid from outside the patient to dislodge the ligating ring includes the step of advancing a controlled dose of pressurized fluid.

17. A ligating method as in claim 15, wherein said instrument has plural releasable ligating rings attached thereto and including the additional steps after step (f) of repeating step (f) one or more times.

18. A ligating method as in claim 15, wherein said instrument has plural releasable ligating rings attached thereto and including the additional steps after step (f) of moving the instrument within the alimentary tract to a second tissue site and repeating steps (c) through (f).

19. A ligating band dispenser for dispensing a plurality of elastic ligating bands onto at least one internal tissue site within a patient's body, comprising:

a body having a proximal portion and a distal portion, the distal portion being adapted to support the plurality of elastic ligating bands;

a tissue contacting surface disposed in surrounding relation to said distal portion and spaced therefrom so as to define a chamber therebetween;

a seal slidably mounted on said distal portion and shaped to seal said chamber;

a fluid inlet proximal to said seal and communicatively coupled with said chamber; and a pressurized fluid delivery device connected in fluid communication with said fluid inlet of said body, said pressurized fluid delivery device being adapted, upon actuation, to deliver to said dispenser a predetermined volume of fluid from a fluid supply, whereby said predetermined volume of fluid from the fluid supply urges said seal distally a distance sufficient to dispense one of the plurality of elastic ligating bands.

* * * * *